United States Patent [19]
Perfect

[11] 4,043,042
[45] Aug. 23, 1977

[54] APPLICATOR FOR TOOTH SEALANT
[75] Inventor: Alan J. Perfect, Allentown, N.J.
[73] Assignee: Johnson & Johnson, New Brunswick, N.J.
[21] Appl. No.: 620,435
[22] Filed: Oct. 7, 1975
[51] Int. Cl.² .............................................. A61C 17/00
[52] U.S. Cl. ...................................... 32/40 R; 128/215
[58] Field of Search ........................... 32/17, 40 R, 60; 128/215, 216, 218 R, 234; 222/386.5

[56] References Cited
U.S. PATENT DOCUMENTS

| 798,093 | 8/1905 | Dean | 128/216 |
|---|---|---|---|
| 1,677,603 | 7/1928 | Steen | 128/216 UX |
| 1,880,354 | 10/1932 | Mueller | 128/216 UX |
| 2,505,028 | 4/1950 | Boeger | 32/17 |
| 2,514,575 | 7/1950 | Hein | 128/218 R |
| 2,595,493 | 5/1952 | Slaby et al. | 128/215 |
| 3,202,319 | 8/1965 | Howard | 222/386.5 X |

Primary Examiner—Robert Peshock

[57] ABSTRACT

The specification describes an applicator for the treatment of teeth with small amounts of polymerizable material. The applicator is in the form of an elongated member having an applicator head which contains a chamber enclosing a similarly-shaped resilient member. A closure fits over the end of the applicator head and serves to close off the base of the chamber and seal the peripheral edge of the resilient member to prevent leakage. The closure is provided with a smaller chamber which communicates with a channel extending out through the closure and adapted to receive a disposable tube. The channel is positioned at an angle to the main body of the applicator. The applicator is provided with a movable lever-operated piston which presses on the resilient member for drawing liquid into and dispensing liquid from a disposable tube after the same has been inserted into the applicator head.

7 Claims, 3 Drawing Figures

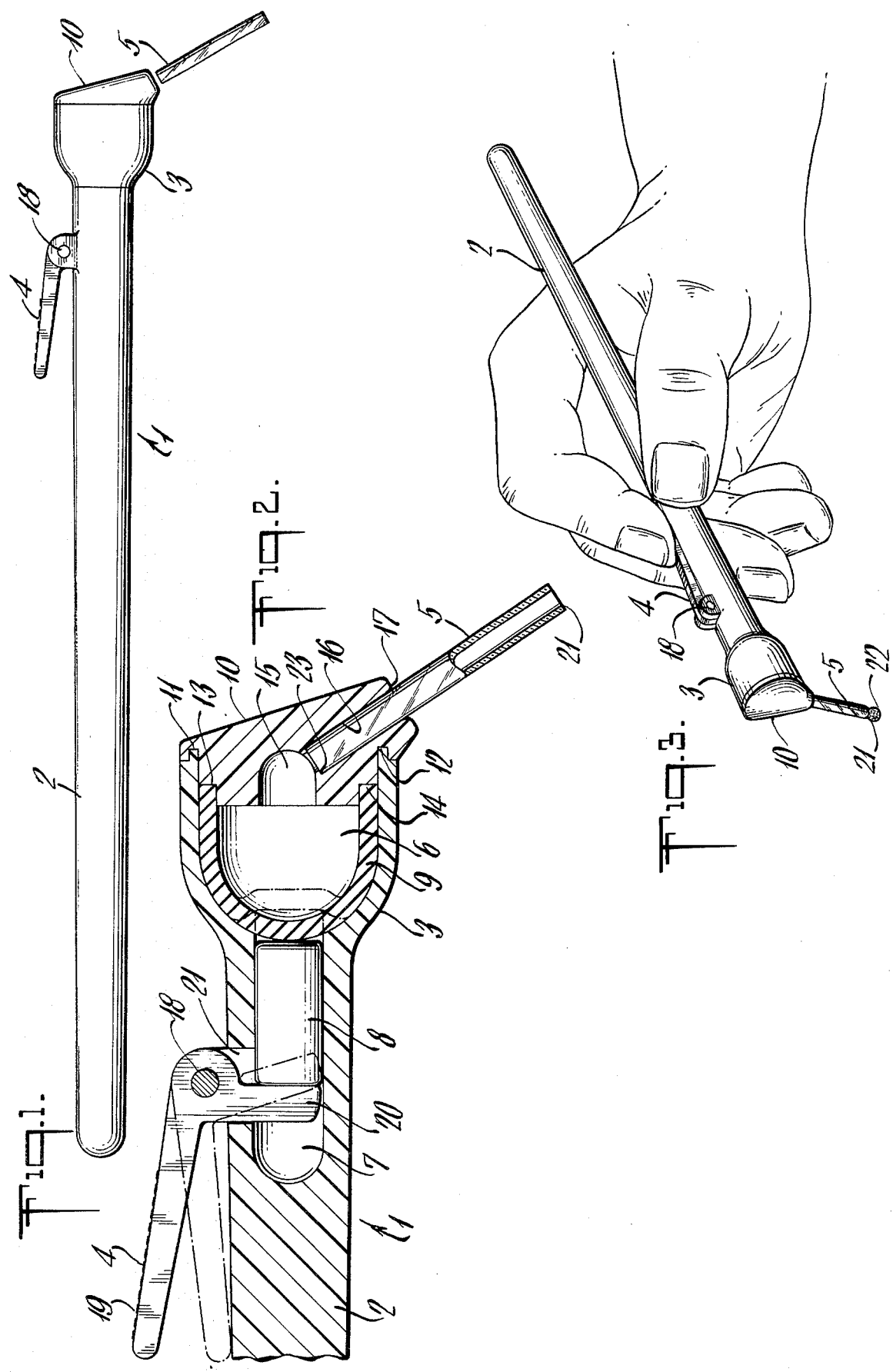

APPLICATOR FOR TOOTH SEALANT

BACKGROUND AND BRIEF DESCRIPTION OF THE INVENTION

There has been increasing interest in the treatment of teeth with fluid polymerizable monomers which are activated to form on the tooth surface, after curing, a strongly adherent protective polymer film coating.

It has generally been the practice to apply these monomeric materials with a brush or spatula to the tooth surface, the polymerizable fluid wetting the surface and tending to flow over the same. Such treatment is awkward at best for the treatment of the upper teeth as the polymerizable monomer, particularly if in a thin fluid state, has a tendency to flow down the applicator making it difficult to apply controlled amounts to the tooth area being treated.

It has heretofore been proposed to use a syringe for applying dental varnishes as shown, for example, in U.S. Pat. No. 2,142,780. However, where the material to be applied has been activated, for example, as the pit and fissure-treating compositions described in U.S. Pat. No. 3,663,501, the activated treating composition remaining in the dispenser would polymerize thus making it necessary to discard the same. As the setting time for such composition, after being activated, is generally in the order of about 5 minutes or less it is apparent that there would not be sufficient time to clean all remaining activated treating composition from a syringe prior to its polymerization.

It has been observed that the best coating of the teeth is obtained when the treating monomer is highly fluid and readily wets the surface of the tooth so as to rapidly flow out over the surface in a thin film. For such treatment it is not only important to carefully position the monomeric coating material on the tooth area to be treated but also to place the coating composition on the tooth in a dropwise maner so that only small quantities are used.

In accordance with the present invention a dispensing applicator is designed which enables the operator to place a drop of activated monomer in a controlled manner on either upper or lower teeth without worry of the activated monomer flowing down the instrument during application. Also, the activated monomer cannot polymerize in the instrument so as to deleteriously effect its operation or reuse. Also, the applicator of the present invention is so designed as to enable the dentist or dental assistant to accurately place a small controlled amount of activated monomer on a tooth surface regardless of its location in the mouth.

The applicator of the present invention is in the form of an elongated member having an applicator head and operating mechanism at one end with the remainder of the elongated member serving as a handle to be grasped by the dentist. A disposable tip, through which the coating composition is applied, is removably carried by the applicator head and projects at an angle with respect to the handle for ease of application.

The applicator head contains a semi-spherical chamber which opens into a relatively short longitudinal first bore contained in the handle portion immediately adjacent to the applicator head. A simultaneously shaped member, such as a cupped resilient diaphram, is positioned in the chamber the diaphram being of such size and shape that its outer surface is adjacent to and preferably contacts the inner surface of the semi-circular chamber.

A closure member positioned on the end of the applicator serves to close the base portion of this first semi-spherical chamber and hold and seal the outer edge of the resilient member. The closure contains a smaller second chamber which is in direct alignment with the longitudinal bore contained in the handle and contains a second bore of somewhat smaller diameter which extends at an angle to the longitudinal axis of the applicator. This second bore extends through the cover and is in direct communication with the second chamber. This second bore contained in the closure member is adapted to receive a disposable tube which is the applicator tip into which treating compositions are drawn and from which applied to the teeth.

The first bore, which is located in the handle portion adjacent applicator head, contains a piston which is adapted to move longitudinally within this first bore and press against the resilient member for compressing the same. An angular-operating lever is pivotally secured on top of the applicator with one leg of the lever extending rearwardly on top of the applicator and essentially paralleling the same with the other leg of the lever extending into the first bore of the applicator and adapted to press on one end of the piston for actuating the same.

When the applicator is to be used, a disposable tube is inserted into the end of the second bore in the applicator head. Pressure is then applied on the exposed leg of the angular-operating lever. This causes the piston to be pushed forward where it presses against the resilient member and expresses air from the semi-spherical chamber. The applicator is then immersed in the activated monomer with which the tooth is to be treated and pressure on the exposed leg of the lever is released. The semi-spherical resilient diaphram then retains its initial form with the result that a partial vacuum is created and air is drawn into the semi-spherical chamber and the liquid up into the disposable tube. The size of the semi-spherical chamber, the distance of movement of the piston, and the diameter and length of the disposable tube are related to each other so that the change in volume in the semi-spherical chamber on movement of the piston is such that only a few drops of liquid are drawn into the disposable tube the amount never being such that the disposable tube will fill and liquid flow into the second chamber inside the closure.

DETAILED DESCRIPTION OF THE INVENTION

For a more detailed description of the applicator, reference is made to the drawings in which:

FIG. 1 is a side view of the applicator;

FIG. 2 is a cross-sectional view of the front portion of the applicator; and

FIG. 3 illustrates how the applicator is held in use.

Referring to the drawings, the applicator 1, is in the form of an elongated member a substantial part of the same forming the handle 2, which would be grasped by the user. This is best illustrated in FIG. 3. The front part of the applicator contains the applicator head 3, the operating lever 4, and the disposable tube 5.

Referring to FIG. 2, the end of the applicator, forming the applicator head, is enlarged as illustrated at 3 to form a semi-spherical first chamber 6. Communicating with this chamber is a first bore 7 containing a piston 8 which is moved by depression of the operating lever 4 so as to press against resilient member 9. The cylindrical member forming piston 8 preferably has an outside diameter of this first bore 7. Also, lever 4, piston 7 and resilient member 9 are all positioned one with respect to the other so that the piston 8 has slight pressure thereon from the resilient member 9 when the operating lever 4 is not being operated. When operated an immediate flexing of the resilient member 9 will take place.

In chamber 6 is positioned a resilient member 9, such as a cupped resilient diaphram, whose outside dimensions are essentially the same as the inside dimensions of chamber 6 so that the outer surface of the diaphram 9 is preferably in contact with the inner surface of chamber 6.

The end of chamber 6 is closed by a closure 10 which is secured to the enlarged portion of the applicator head 3 by means of a flange 11 extending from the end of enlarged portion 5 and adapted to fit snugly into a groove 12 provided in the closure 10. The outer periphery 13 of the semi-spherical resilient member 9 is held in sealed position in the recess 14 formed between the inner surface of the enlarged portion of the applicator head 3 and the closure 10.

Closure 10 contains a second chamber 15, smaller than the first chamber 6 and in substantially direct longitudinal alignment with the first bore 7. A second bore or channel 16 extends downwardly from this chamber 15 through closure 10 at a substantial angle to the longitudinal axis of the applicator and is adapted to have the disposable tube 5 inserted therein prior to use of the applicator. The outer end 17 of bore 16 is beveled to aid in the insertion of disposable tube 5. In order to avoid an inserted disposable tube 5 from entering second chamber 15 the inner diameter of the second bore 16 is reduced at 23 so as to provide a stop for the disposable tube 5.

The operating lever 4 is an angular member pivotally attached at 18 with one leg 19 extending outside of the applicator lengthwise of the same and the other leg 20 extends down into the bore 7. Leg 19 is raised from the surface of the applicator so that the same can be depressed. A cut-away portion 21, is provided to permit forward movement of the leg 20 when leg 19 of the lever 4 is pressed downwardly.

When leg 19 of lever 4 is pressed, lever 4 will pivot around pivot 18 with the leg 20 of lever 4 moving forward. The forward movement of leg 20 causes piston 8 to be pushed along bore 7 and press against the outer periphery of the resilient diaphram 9. In the preferred embodiment the legs 19 and 20 of the lever are of such length and so disposed with respect to each other that substantial finger movement for operating the lever is required for slight forward movement to be transmitted to the piston, this movement generally being on a ratio of about two to one.

The purpose of using the piston 8 for pressing on the diaphram 9 rather than having the leg 20 press directly thereon is that through use of the piston 8 a substantially more controlled and uniform pressure can be obtained. Also, the reason for having the resilient diaphram 9 fit snugly within the semi-spherical chamber 6 is to obtain more uniform action. Uniform action is important as the device is designed for applying small controlled amounts of material in a uniform manner.

In use, the dentist or dental assistant will insert a disposable tube 5, from a quantity made available, into opening 17. He will then prepare the treating composition which, if a pit and fissure sealant, will be a catalyzed monomer or monomer mix which will polymerize after a few minutes depending on the particular set time for the material used. The dentist or dental assistant would then depress lever 4, place the exposed end or tip 21 of the disposable tube 5 in the prepared composition, release pressure on lever 4 and then apply the tip 21 to the tooth to be treated. The lever 4 would then again be depressed with the result that a small amount 22 of the treating composition would be forced out through tip 5.

The internal diameter of disposable tube 5 is relatively small as the applicator is designed for applying small controlled quantities of fluid, preferably in a droplike manner. Also, the movement of the piston 8 with respect to the diaphram 9 is adjusted so that the partial vacuum created when the pressure of lever 4 on piston 8 is released and the diaphram permitted to return to its original position, is such that the volume of fluid drawn into the disposable tube 5 is insufficient to completely fill the tube. Thus, any spilling of the treated fluid into the chamber 15 is avoided. After treatment of several teeth the dentist or dental assistant would then remove the disposable tube 5 and discard the same. A new tube 5 would then be inserted into the applicator head prior to further use. It is thus apparent that none of the treating composition would remain in the applicator, and any problems resulting from polymerization of the treating composition in the applicator is thus avoided In one preferred embodiment of the applicator the space within the chamber formed by resilient member 9 has a volume of about 0.0297 cubic inches. The disposable tubes used are of ¾ or ⅝ inch in length and have inside diameters of 0.062 and 0.0018 inches respectively. Thus, the inside volume of the ¾ inch tube is 0.0023 cubic inch and that of the ⅝ inch tube 0.0018 cubic inch.

The movement of the piston 8 on depression of the operating lever is adjusted so as to only partially fill the disposable tube with treating liquid on release of the operating lever.

Although the applicator has been described for use primarily with pit and fissure sealants, the same may be used for applying other treating materials to tooth surfaces. The particular construction described enables the applicator head to be relatively small in size while still obtaining controlled and efficient operation with the actuator lever being in position for convenient and efficient control by the operator. Also, the angular position of the disposable tube with respect to the remainder of the applicator, the positioning of the operating lever with respect to the applicator head and the relatively small dimensions of the applicator head all enable the operator to work in the patient's mouth in any position and obtain excellent access to otherwise difficult tooth areas.

What is claimed is:

1. An applicator for dispensing a small amount of a polymerizable fluid on tooth surfaces comprising:
    an elongated member,
    a first bore formed in the forward end of said elongated member,
    a first chamber formed in the forward end of said elongated member and in direct communication with said first bore,
    a resilient diaphragm positioned in said first chamber,
    movable means in said first bore positioned with respect to said resilient diaphragm as to maintain positive pressure thereon,
    a closure for said first chamber, a second chamber in said closure said second chamber being in communication with said first chamber, a second bore in said closure said second bore extending from said second chamber and through said closure at an angle to the longitudinal axis of said elongated member and adapted to have a disposable tube inserted therein, and operating means for moving said movable means towards said resilient diaphragm to increase the pressure thereon and expel air from said first chamber, the relative size of said first chamber and the distance of movement of said movable means is such that the change in volume of the first chamber on movement of the movable means away from said resilient diaphragm is such that only a few drops of liquid are drawn into the tube and no liquid is allowed to enter the chambers.

2. An applicator of claim 1 wherein said first chamber and said resilient diaphram have a substantially semispherical configuration.

3. An applicator of claim 2 in which the outer surface of said resilient diaphram has substantially the same configuration as the inner surfaces of said first chamber and the surfaces are normally in substantial contact with each other.

4. An applicator of claim 1 in which said second bore has restraining means to prevent a tube inserted therein from entering said second chamber.

5. An applicator of claim 1 in which said movable means is in the form of a piston.

6. An applicator of claim 5 in which said operating means is a pivoted lever having two legs one extending outside of said elongated member and the other extending into said first bore and in contact with one end of said cylindrical movable means.

7. An applicator for dispensing a small amount of a polymerizable fluid on a tooth surface comprising:

an elongated handle having an upper and a lower surface, a relatively small applicator head at one end of said elongated handle, an air chamber in said applicator head, resilient means associated with said air chamber for expelling air from and drawing air into said applicator head, actuator means for moving said resilient means with a portion of said actuator means extending above the surface of said handle and adapted to be actuated by finger pressure thereon said actuator means being positioned close to said applicator head and within about two inches distance from the end of said applicator and a channel extending through the end of said applicator head in communication with said air chamber said channel extending downwardly with respect to the lower surface of said applicator handle and at an obtuse angle thereto said channel adapted to have inserted therein a disposable tube.

* * * * *